United States Patent [19]

Jóvér et al.

[11] Patent Number: 5,744,629
[45] Date of Patent: Apr. 28, 1998

[54] PROCESS FOR MANUFACTURING METHYLENE-BIS (DIBUTYL-DITHIOCARBAMATE) WITH ASTM COLOUR LESS THAN 2

[75] Inventors: Béla Jóvér, Budapest; János Forstner, Százhalombatta; József Petró, Százhalombatta; Szabolcs Szoboszlay, Százhalombatta; Imre Fekete, Százhalombatta; Károly Csergo, Százhalombatta; Gyula Sztrehárszki, Százhalombatta; Gyula Ráksi, Százhalombatta; János Kiss, Almásfúzitó; Ferenc Mikó, Komárom; JenóBaladincz, Komárom; József Tóth, Komárom, all of Hungary

[73] Assignee: MOL Magyar Olaj- es Gazipari Rt., Szazhalombatta, Hungary

[21] Appl. No.: 595,286

[22] Filed: Feb. 2, 1996

[30] Foreign Application Priority Data

Feb. 20, 1995 [HU] Hungary ................. P9500320

[51] Int. Cl.$^6$ ................................ C07C 57/04
[52] U.S. Cl. ................................ 562/28
[58] Field of Search ................................ 562/28

[56] References Cited

U.S. PATENT DOCUMENTS 3,725,443   4/1973   Horiie et al. .
4,967,007   10/1990  Deshmukh et al. .
5,015,368   5/1991   Di Biase et al. .

Primary Examiner—Samuel Barts
Attorney, Agent, or Firm—Keil & Weinkauf

[57] ABSTRACT

The invention relates to improved manufacture of methylene bis-(dibutyl-dithiocarbamate) with ASTM coulour less than 2, by reacting aqueous solutions of dibutyl amine and sodium hydroxide with carbon disulfide, treating the obtained reaction product with methylene dichloride, followed by vacuum stripping, phase separation and filtration of the precipitated sodium chloride. According to the invention, during reaction with carbon disulfide the temperature of the mixture is kept at or below 15° C. and the vacuum stripping is performed in two steps, first between 45° C. and 100° C. and at a pressure of 5–50 kPa, then phase separation is carried out at a temperature between 35° C. and 50° C., followed by stripping the separated organic phase in vacuum also at a temperature between 45° C. and 100° C. and at a pressure of 5–50 kPa.

2 Claims, No Drawings

PROCESS FOR MANUFACTURING METHYLENE-BIS (DIBUTYL-DITHIOCARBAMATE) WITH ASTM COLOUR LESS THAN 2

This invention relates to improved manufacture of methylene-bis(dibutyl-dithiocarbamate) with ASTM colour less than 2, by reacting aqueous solutions of dibutyl amine and sodium hydroxide with carbon disulfide, treating the obtained reaction product with methylene dichloride, followed by vacuum stripping, phase separation and filtration of the precipitated sodium chloride.

4,4'-Methylene-bis(dibutyl-dithiocarbamate) is a widely used ashless antioxidant and an extreme pressure (EP) additive. Due to its advantageous properties it is utilized in a lot of petroleum-based products (lubricants, asphalt and other products).

As an additive, it has several trade names such as DITIO-9, VANLUBE 7723 or KOMAD 503.

It is prepared by a two-step synthesis. In the first step, NaOH and dibutyl amine are reacted in an aqueous solution yielding sodium salt of N,N'-dibutyl-dithiocarbamic acid:

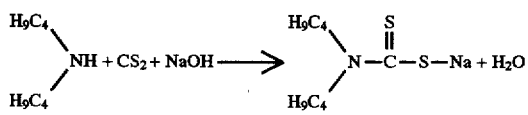

In the second step this sodium salt is coupled with methylene dichloride to the end product:

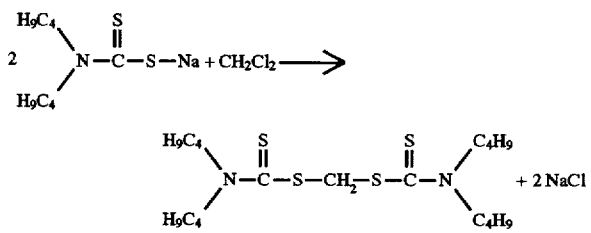

Several patents describe procedures for realization of the above synthesis in a 0.5–2.0 kg range of production.

According to U.S. Pat. No. 3,876,550, a product of acceptable quality can be prepared in a 1.5 mole (approximately 500 g) size, if 627 g of dibutyl amine, 240 g of 50% aqueous solution of sodium hydroxide, 200 g of toluene and 200 g of isopropanol are mixed and over 5 hours 228 g of carbon disulfide are slowly added. The temperature of the mixture should be kept at or below 42° C. Having performed the reaction, the mixture is slowly heated up to 65° C., when the non-reacted carbon disulfid distils out. Then, over 2.5 hours, 225 g of methylene dichloride are added, meanwhile the temperature raises to 75° C. After the addition of methylene dichloride, the temperature of the mixture is kept at 60°–65° C. for further 2.5 hours. This is followed by washing three times with 150 ml of water in each case. Devolatilization takes place by vacuum stripping at 122° C. and 120 mm of Hg pressure. The precipitated sodium chloride is separated from the product by filtration.

According to U.S. Pat. No. 5,015,368 1000 g of dibutyl amine are mixed with 650 g of a 50% aqueous solution of NaOH. After dilution with 1356 g of water, 603 g of $CS_2$ are slowly added. The allowable upper limit of temperature is 65° C. In a second step, 363 g of methylene dichloride are added over 4 hours, meanwhile the temperature raises to 88° C. The mixture is kept at this temperature for further three hours. Then stirring is stopped and the aqueous phase is separated. The rest of the mixture is stripped at 150° C. and 50 mm of Hg pressure and filtered.

As it is apparent from the cited literature, conditions of mixing and heat transfer are essential during addition of $CS_2$ and methylene dichloride. That is the reason why both components are to be added slowly and an upper limit of temperature is to be kept.

In the course of our work we intended to manufacture methylene-bis(dibutyl-dithiocarbamate) in the range of at least 300 kg batch size. For this reason, we have tried to reproduce the procedures described in the above-mentioned U.S. patents. It turned out, however, that in this batch size, these procedures give very poor results. The yield was below 40%, the product contained 150–200 ppm of NaCl and its ASTM colour (as measured according to ASTM D 1500 Standard) was higher than 5, i.e. beyond the upper limit of the scale. We have stated that, as it is expectable, with greater batch sizes the conditions of mixing and heat transfer are more unfavourable and tenside-like side products may form, which hinder the separation of the product mixture into aqueous and organic phases and also hinder separation of NaCl by filtration.

It is an object of the present invention to eliminate draw-backs of former art and to elaborate a procedure by which methylene-bis(dibutyl-dithiocarbamate) can be manufactured in a high yield and with an ASTM colour less than 2.

Economic advantages of high yield are evident. In this case, we should add, moreover, environmental considerations, too. Non-reacted amine or carbon disulfide are harmful wastes, thus a high yield is desirable from this point of view as well. Colour of the product is not prescribed by any standard but in practice, the lighter the product the better is its value. This is reasonable, since deviation of the colour from water-like, colourless state is caused by side-products of indefinable composition. Taking into account that the product is used in additives which have to protect lubricants and other compositions for a long time, it is understandable that the presence of any contamination of undefinable composition decreases its reliable life expectancy. As to the NaCl content of the product, it is acceptable below approximately 100 ppm.

It has now been discovered that formation of tenside-like side-products can be significantly suppressed if during addition of carbon disulfide, the temperature of the mixture is kept at or below 15° C., vacuum stripping is performed in two steps, first between 45° C. and 100° C. and 5–50 kPa pressure, which is followed by a phase separation, whereafter the separated organic phase is vacuum stripped again, also between 45° C. and 100° C. and at 5–50 kPa pressure.

It has also been discovered that a small fraction of tenside-like side-products does not leave during the first vacuum stripping. It has also been discovered that these side-products can be eliminated if the phase separation is performed within an optimized range of temperature, namely between 35° C. and 50° C.

In the light of the foregoing, the invention relates to an improved process for the manufacture of methylene-bis (dibutyl-dithiocarbamate) which, for the first time, provides direct access to the large-scale commercial product with an ASTM colour less than 2, and which is based upon the reaction of dibutyl amine and carbon disulfide with NaOH in an aqueous solution, and treatment of the obtained mixture with methylene dichloride, followed by vacuum stripping, phase separation and filtration of the precipitated NaCl. The process comprises the steps of keeping the temperature of the mixture during the reaction with carbon disulfide at or below 15° C. and performing the vacuum stripping in two steps, first at a temperature between 45° C. and 100° C. and at a pressure of 5–50 kPa, then carrying out the phase separation between 35° C. and 50° C., and thereafter performing the second vacuum stripping of the separated organic phase also at a temperature between 45° C. and 100° C. and at a pressure of 5–50 kPa.

According to the present invention, a greater part of the tenside-like side-products leaves during the first vacuum stripping, and the bottom can be phase-separated into an aqueous and an organic phase. Following this step, the organic phase can be fully devolatilized by a second vacuum stripping.

As compared to the prior art, the present invention provides the following main advantages:

a) The quality of the product is better than that of the products manufactured according to the prior art, since its ASTM colour is less than 2. Until now, there was no procedure providing direct access to a large-scale commercial product with an ASTM colour less than 2.

b) The NaCl content of the product is very low, it is below 40 ppm.

c) The yield is very high, it is above 95%, of the theoretical value.

The invention will be further illustrated by the following examples that set forth particularly advantageous embodiments. While the Examples are provided to illustrate the present invention, they are not intended to limit it.

EXAMPLE 1

64 kg of NaOH, 206.8 kg of dibutyl amine, and 416 kg of water were mixed in a 1 m³ autoclave and the mixture was cooled to 5° C. while stirring. Maintaining stirring, 121.6 kg of carbon disulfide were slowly added to the cooled mixture. The temperature was controlled by an effective cooling system and it was not allowed to raise above 15° C. After addition of the carbon disulfide, stirring was continued for 0.5 hour, while keeping the temperature at or below 15° C. Then 81.6 kg (20% excess) of methylene dichloride were added and the autoclave was slowly heated. Alkylation, which is a highly exothermic process, started at 45° C. Heat of reaction was taken off by the reflux of methylene dichloride. In the course of reaction, the temperature of the autoclave raised to 75°–80° C. A 2-hour after-treatment took place at this temperature.

After alkylation, the excess of methylene dichloride was distilled off at normal pressure and it was followed by a vacuum distillation at 7 kPa pressure, to a pot temperature of 55° C. In this step 80 kg of water distilled out, together with rest of non-reacted starting materials and formed side-products. After vacuum distillation, the autoclave was cooled to 40°±2° C., which resulted in separation of the mixture into an aqueous and an organic phase. The masses of the upper, organic phase and the lower, aqueous phase were 338 kg and 538.4 kg, respectively. After separation of the aqueous phase, the organic phase was further distilled in vacuum at a pressure of 7 kPa, to a pot temperature of 60° C., and in this way another 20 kg of water were distilled out. This fraction contained tenside-like substances.

The remained 318 kg organic phase was washed three times with 320 kg water each at a temperature of 40°±2° C. Each washing was followed by a 0.5-hour sedimentation and phase separation.

This procedure resulted in an amber-coloured product with 15 ppm NaCl content. The ASTM colour was 1. The yield was 98.2%.

EXAMPLE 2

The procedure of Example 1 was used with the only difference that the second vacuum stripping was performed at 40 kPa pressure to a pot temperature of 90° C. The procedure resulted in an amber-coloured product with 35 ppm NaCl content. The ASTM colour was 1. The yield was 96.5%.

EXAMPLE 3

The procedure of Example 1 was used with the following differences: the first vacuum stripping was performed at 10 kPa pressure to a pot temperature of 60° C. In this step, together with non-reacted starting materials and side-products, 60 kg of water were taken off. The temperature of phase separation was 45° C. and the second vacuum stripping was performed at 35 kPa pressure to a pot temperature of 70° C.

This procedure resulted in an amber-coloured product with 20 ppm NaCl content. The ASTM colour was 1.5. The yield was 97.8%.

EXAMPLE 4

The procedure of Example 1 was used with the following differences: during addition of carbon disulfide the temperature was kept below 12° C. The first vacuum stripping was performed at 10 kPa pressure to a pot temperature of 60° C. The temperature of phase separation was 45° C.

This procedure resulted in an amber-coloured product with 30 ppm NaCl content. The ASTM colour was 1.5. The yield was 96.6%.

EXAMPLE 5

The procedure of Example 1 was used with the following differences: during addition of carbon disulfide the temperature was kept below 10° C. The first vacuum stripping was performed at 45 kPa pressure to a pot temperature of 90° C. The temperature of phase separation was 36° C.

This procedure resulted in an amber-coloured product with 24 ppm NaCl content. The ASTM colour was 1.5. The yield was 97.6%.

COMPARATIVE EXAMPLE 1

Using the procedure of U.S. Pat. No. 3,876,550, 80 kg of a 50% aqueous solution of NaOH, 209 kg of dibutyl amine, 66.6 kg of toluene and 66.6 kg of isopropyl alcohol were mixed in a 1 m³ autoclave. During 5 hours 76 kg of carbon disulfide were added to this mixture, meanwhile the temperature elevated to 40° C. After this period, for elimination of non-reacted carbon disulfide, the mixture was heated slowly to 65° C. With 15° C. condenser temperature, no distillate was obtained.

Then, during 2.5 hours, 75 kg of methylene dichloride were added and the mixture was after-reacted for further 2.5 hours at 60°–65° C. Before phase separation, the mixture stood for 4 hours, but only 10% of the aqueous phase could be separated. The main body of of reaction mixture remained a viscous, gum-like emulsion. It was washed three times with 50 l of water each. In the course of this treatment, the emulsion took up 44–46% of the washing water.

The volatiles were removed by vacuum stripping to a pot temperature of 105° C. at 16 kPa pressure. As a result of this procedure, first 230 kg of ill-smelling water, contaminated with toluene and isopropyl alcohol, distilled out. Continuing vacuum distillation, between 105° C. and 127° C. 142 kg of malodorous side products with an indefinite composition were obtained. The remained, devolatilized product was filtered using a ceramic filter-pipe. The process of filtering took 8 hours.

The yield was 39%. The NaCl content of the product—in spite of the lengthy filtering—was between 150 and 200 ppm and its colour was opalescent black. In the course of study of solubility in oil, 5–8% sedimentation was observed.

COMPARATIVE EXAMPLE 2

The procedure of Comparative Example 1 was used with the following differences: in the course of addition of carbon disulfide the temperature was kept below 15° C. It resulted in formation of a smaller amount of side-products and 40% of the aqueous phase could be separated. While washing with 3×50 l of water only 20% of the washing water built in into the organic phase. During devolatilization at 16 kPa pressure to a pot temperature of 105° C., 195 kg of an aqueous fraction, containing toluene and isopropyl alcohol, were obtained and the mass of the second fraction was 15% less than that in Comparative Example 1. The yield increased to 55%, the filtration became less time-consuming, it needed only 6 hours, and the NaCl content of the product diminished to 120 ppm. ASTM colour of the product was between 4.5 and 5.

COMPARATIVE EXAMPLE 3

We have used the procedure of Comparative Example 1, with the following differences: after alkylation, the devolatilization was performed in two steps and phase separation was performed at ambient temperature.

After devolatilization, 60 kg of starting materials and ten-side-like side products were taken off, first by atmospheric, then by vacuum distillation. Following this step, phase separation could be performed with a 90% efficiency. In the course of washing with 3×50 l of water, it was only 6–8% of the water that built in into the organic phase. Elevated temperature of phase separation resulted in a more definite phase boundary and more perfect separation of the phases. The yield increased to 83%, and NaCl content of the product diminished below 50 ppm. ASTM colour of the product was between 2.5 and 3.

The comparative Examples 1 to 3 clearly demonstrate that, as it has been discovered in the present invention, it is essential that during reaction with carbon disulfide the temperature be kept at or below 15° C., vacuum stripping be performed in two steps, and the phase separation be performed between 35° C. and 50° C. These conditions result in a product of better quality (of smaller ASTM colour) and with a higher yield than those applied in the prior art.

We claim:

1. An improved process for manufacturing methylene-bis-(dibutyl-dithiocarbamate) with ASTM colour less than 2, by reacting aqueous solutions of dibutyl amine and sodium hydroxide with carbon disulfide, treating the obtained reaction product with methylene dichloride followed by vacuum stripping, phase separation and filtration of the precipitated sodium chloride, which comprises keeping the temperature of the mixture during the reaction with carbon disulfide at or below 15° C. and performing the vacuum stripping in two steps, first at a temperature between 45° C. and 100° C. and at a pressure of 5–50 kPa, then carrying out the phase separation between 35° C. and 50° C., and thereafter performing the second vacuum stripping of the separated organic phase also at a temperature between 45° C. and 100° C. and at a pressure of 5–50 kPa.

2. The process of claim 1, in which both steps of said vacuum stripping are performed at a temperature between 50° C. and 70° C. and at a pressure of 7–12 kPa and said phase separation is carried out at a temperature between 40° C. and 45° C.

* * * * *

UNITED STATES PATENT AND TRADEMARK OFFICE
CERTIFICATE OF CORRECTION

PATENT NO.: 5,744,629

DATED: April 28, 1998

INVENTOR(S): JÓVÉR et al.

It is certified that error appears in the above-identified patent and that said Letters Patent is hereby corrected as shown below:

In the title page, item [30], "Feb. 20, 1995" should be --Feb. 3, 1995--.

Signed and Sealed this

Fourth Day of August, 1998

Attest:

BRUCE LEHMAN

Attesting Officer

Commissioner of Patents and Trademarks